(12) United States Patent
Brandner et al.

(10) Patent No.: US 10,682,621 B2
(45) Date of Patent: Jun. 16, 2020

(54) PLANT AND PROCESS FOR PRODUCING FATTY ALCOHOL

(71) Applicant: L'Air Liquide, Societe Anonyme pour l'Etude et l'Exploitation des Procedes Georges Claude, Paris (FR)

(72) Inventors: Armin Brandner, Egelsbach (DE); Manfred Hoffmann, Wehrheim (DE); Fredrik Pomrehn, Frankfurt am Main (DE); Peter Potschacher, Frankfurt am Main (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 15/773,698

(22) PCT Filed: Oct. 14, 2016

(86) PCT No.: PCT/EP2016/025117
§ 371 (c)(1),
(2) Date: May 4, 2018

(87) PCT Pub. No.: WO2017/076505
PCT Pub. Date: May 11, 2017

(65) Prior Publication Data
US 2018/0318783 A1    Nov. 8, 2018

(30) Foreign Application Priority Data

Nov. 6, 2015 (EP) ..................................... 15400052

(51) Int. Cl.
*B01J 8/04* (2006.01)
*C07C 29/149* (2006.01)
*B01J 8/00* (2006.01)

(52) U.S. Cl.
CPC ........... *B01J 8/0457* (2013.01); *B01J 8/0035* (2013.01); *C07C 29/149* (2013.01); *B01J 2219/00006* (2013.01); *B01J 2219/00033* (2013.01); *B01J 2219/185* (2013.01); *B01J 2219/1943* (2013.01); *Y02P 20/582* (2015.11)

(58) Field of Classification Search
CPC ............ B01J 8/0457; B01J 2219/00006; B01J 2219/185; B01J 2219/1943; B01J 2219/00033; B01J 8/0035; C07C 29/149; Y02P 20/582
See application file for complete search history.

(56) References Cited

U.S. PATENT DOCUMENTS

| | | | |
|---|---|---|---|
| 4,185,967 A | | 1/1980 | Komodromos et al. |
| 5,192,132 A | * | 3/1993 | Pelensky ................. B01J 8/003 136/230 |
| 2007/0225527 A1 | | 9/2007 | Wuerkert et al. |
| 2009/0026111 A1 | * | 1/2009 | Garton ...................... B01J 8/02 208/49 |
| 2009/0156846 A1 | * | 6/2009 | Seki ........................ C07C 67/03 554/170 |
| 2013/0072717 A1 | | 3/2013 | Olbert et al. |

FOREIGN PATENT DOCUMENTS

| | | |
|---|---|---|
| DE | 198 43 798 | 3/2000 |
| WO | WO 02/100807 | 12/2002 |

OTHER PUBLICATIONS

International Search Report and Written Opinion for PCT/EP2016/025117, dated Feb. 1, 2017.

* cited by examiner

*Primary Examiner* — Rosalynd A Keys
(74) *Attorney, Agent, or Firm* — Jason K. Murray

(57) ABSTRACT

A plant and a process for carrying out the continuous production of fatty alcohol from fatty acid ester by catalytic trickle-bed hydrogenation, comprising shaft reactors each containing at least one catalyst fixed bed, which are connected with each other via pipe conduits such that they can be traversed by the educt/product mixture one after the other, in freely selectable order.

6 Claims, 1 Drawing Sheet

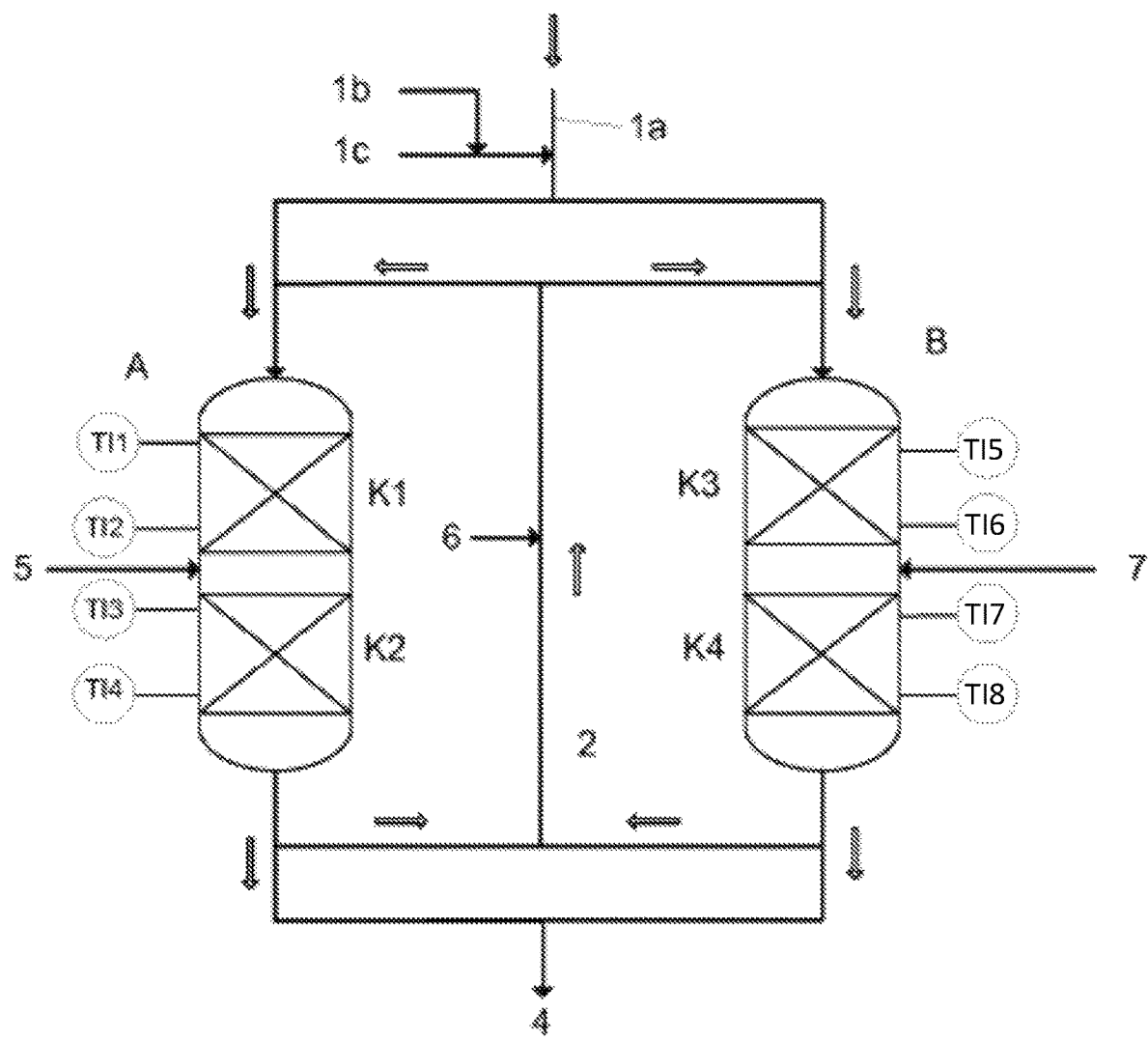

PLANT AND PROCESS FOR PRODUCING FATTY ALCOHOL

CROSS REFERENCE TO RELATED APPLICATIONS

This application is a § 371 of International PCT Application PCT/EP2016/025117, filed Oct. 14, 2016, which claims the benefit of EP15400052.5, filed Nov. 6, 2015, both of which are herein incorporated by reference in their entireties.

FIELD OF THE INVENTION

This invention relates to a plant for carrying out a continuous process for the production of fatty alcohol from fatty acid ester by catalytic trickle-bed hydrogenation, comprising a plurality of shaft reactors each containing at least one catalyst fixed bed, which are connected with each other via pipe conduits such that they can be traversed by the educt/product mixture one after the other.

This invention furthermore comprises a process for operating the plant.

BACKGROUND OF THE INVENTION

Such plants and processes are known. In Ullmann's Encyclopedia of Industrial Chemistry, Sixth Edition, Vol. 13, page 115, this process is described in principle as "trickle-bed hydrogenation". Under elevated pressure and at elevated temperature, the fatty acid ester to be converted here is mixed in liquid form with gaseous hydrogen stoichiometrically added in excess to obtain an educt mixture. The educt mixture is passed over a catalyst fixed bed, which also can be referred to as trickle bed, wherein the educt mixture is converted into a product mixture consisting of fatty alcohol, hydrogen and, depending on the fatty acid ester used, also of further alcohols. The product mixture is cooled to a temperature in the range from 40 to 80° C., preferably 60 to 80° C. Then, the hydrogen and highly volatile components are separated from the product mixture. The liquid fatty alcohol is discharged from the plant as product for the further use. The hydrogen is recirculated to the beginning of the process, where it is combined with fresh hydrogen and reused for forming the educt mixture.

For carrying out the catalytic conversion, the educt mixture is charged to the catalyst fixed bed (trickle bed) with a temperature in the range from 150 to 250° C., preferably 180 to 250° C. The hydrogenation proceeds exothermally, wherein a too strong rise of the temperature of the educt/product mixture must be avoided, in order to keep the formation of undesired by-products as low as possible.

In the German patent specification DE 198 43 798 C2 a process variant therefore is proposed, in which quench hydrogen is introduced into the catalyst fixed bed to limit the rise in temperature. The quench hydrogen is obtained by branching off one part of the cooled hydrogen separated from the product mixture as "quench hydrogen". The remaining hydrogen, mixed with fresh hydrogen, is recirculated to the beginning of the process as cycle hydrogen and used to form the educt mixture. It also is proposed there to split up the catalyst fixed bed and arrange it in two series-connected reactors and in the process likewise feed quench hydrogen into the transfer conduit between the reactors for the educt/product mixture.

In these plant and process concepts it is disadvantageous that the plant must be shut down to exchange the catalyst whose effect decreases after a certain operating time. It furthermore is disadvantageous that the effectiveness of the bottommost part of the catalyst bed cannot fully be utilized.

DESCRIPTION OF THE INVENTION

It therefore is the object of the present invention to provide a plant and a process which overcome the disadvantages of the prior art. This object is solved by the invention corresponding to the features of the independent claims by the plant and the process according to the invention.

Plant According to an Embodiment of the Invention:

A plant for the continuous production of fatty alcohol from fatty acid ester, in particular wax ester, by catalytic trickle-bed hydrogenation, comprising supply conduits for the fatty acid ester and hydrogen, a discharge conduit for the liquid product mixture containing fatty alcohol, a return conduit for non-converted hydrogen and several, preferably two, shaft reactors each containing at least one catalyst fixed bed, which are connected with each other via pipe conduits such that they can be traversed by the educt/product mixture one after the other, wherein the reactors are connected with each other by pipe conduits such that a) the order in which the reactors are traversed by the educt/product mixture is freely selectable, and
b) each reactor also can each be traversed alone, by bypassing the respective other reactor, and
c) each of the reactors is designed with respect to the one or more catalyst fixed beds contained therein such that at a specified production output of the plant the required degree of conversion of the educts can be achieved with the passage through only one of the reactors at least for the duration of an exchange of the one or more catalyst fixed beds in the respective other reactor.

Process According to an Embodiment of the Invention:

A process for the continuous production of fatty alcohol from fatty acid ester, in particular wax ester, by catalytic trickle-bed hydrogenation, comprising the following process steps:

a) providing fatty acid ester and fresh and recirculated hydrogen,
b) producing an educt mixture of fatty acid ester and hydrogen at a pressure in the range from 50 to 250 bar, preferably 75 to 100 bar,
c) heating of the mixture to a temperature in the range from 150 to 250° C., preferably 180 to 250° C.,
d) passing of the mixture through a first and then through a second shaft reactor, which each contain at least one catalyst fixed bed designed as trickle bed, wherein the educt mixture is converted into a product mixture which contains fatty alcohol, hydrogen and, depending on the fatty acid ester used, also further alcohols,
e) cooling of the product mixture,
f) separation of the hydrogen from the liquid product mixture containing fatty alcohol,
g) recirculation of the hydrogen for use in step b),
h) discharging the liquid product mixture containing fatty alcohol from the process for the further treatment,
wherein the exchange of the catalyst is effected without interruption of operation, in that in step d) traveling of the reaction zone through the catalyst fixed beds of the shaft reactors is observed by determining the respective temperature profile forming along the bed length and varying in time and, when the reaction zone has passed over from the first into the second reactor and when traveling of the reaction zone in the second reactor has progressed to such an extent that an inactive zone has formed above the same in the catalyst fixed bed, its length is sufficient to serve as protection zone for trapping catalyst poisons, the first reactor is put out of operation by introducing the mixture from step c) directly into the second reactor, that the consumed catalyst in the first reactor is replaced by fresh catalyst, and the reactor is again put into operation in that it is connected downstream of the other reactor.

In normal production operation the plant is operated such that two series-connected reactors are traversed by the educt/product mixture. The hydrogenation is effected at the beginning of the operating time of the plant filled with fresh catalyst in the first one of the reactors. In the course of the operating time of the catalyst bed the reaction zone, i.e. the zone in which the hydrogenation reactions take place, travels through the bed from top to bottom. The deactivated, i.e. consumed part of the catalyst, lying above the reaction zone, acts as protective zone for the still active catalyst, in that it traps catalyst poisons. By means of temperature measuring devices distributed along the length of the catalyst bed it can be observed how the reaction zone in the catalyst bed travels through the bed in the course of the operating time. When the reaction zone has reached the lower region of the catalyst bed in the first reactor, it gradually starts to pass over into the initial region of the bed arranged in the second reactor. When the reaction zone has completely passed over into the second reactor and when a layer of deactivated catalyst has formed there in the upper part, i.e. in the entry part of the catalyst bed, the first reactor is shut down. The formation of a layer of deactivated catalyst is waited for, as it serves as protective layer against catalyst poisons. How long this protective layer must be, in order to be sufficiently effective, must be found out by operational experiments.

To exchange the catalyst of the first reactor, the educt/product mixture only is passed over the second reactor. After exchange of the catalyst the reactors, in reverse order, are again connected in series and traversed one after the other. In this way, the catalyst is utilized completely along the entire length of the bed and the exchange of the consumed catalyst can be effected without interruption of operation. In addition, this arrangement of two series-connected reactors also ensures that even if the reaction zone passes over from the first into the second reactor, the educt/product mixture always flows first through a protective layer of deactivated catalyst, before it reaches the reaction zone.

Outside the plant and the process according to the invention excess hydrogen not consumed during the hydrogenation is separated from the product in a mechanical way and recirculated into the plant for reuse.

Preferred Aspects of the Invention

A preferred aspect of the invention is characterized in that the plant and the reactors are designed such that below the one or more catalyst beds and/or into the transfer conduit between the reactors quench hydrogen can be fed. Quench hydrogen is hydrogen whose temperature, for example 75° C., lies distinctly below the temperature at which the hydrogenation is carried out. By feeding said hydrogen according to claim 2, the temperature rise in the reactors can be limited.

Another preferred aspect of the invention is characterized in that it comprises a depressurizing device which is connected with the supply conduit for the fatty acid ester. The depressurizing device can be equipped with a system for sucking off gases and/or vapors, by which a pressure between 1 and 1000 mbar, preferably between 10 and 700 mbar is generated therein. Such device is particularly advantageous when the fatty acid ester is a wax ester. By using the depressurizing device the content of free fatty acids and other components of higher volatility as compared to the wax ester in the fatty acid or wax ester can be reduced.

BRIEF DESCRIPTION OF THE DRAWINGS

Further features, advantages and possible applications of the invention can also be taken from the following description of exemplary embodiments and numerical examples as well as the drawing. All features described and/or illustrated form the subject-matter of the invention per se or in any combination, independent of their inclusion in the claims or their back-reference.

The FIGURE shows a schematic diagram of the connection of two catalyst-filled fixed-bed reactors of a plant according to an embodiment of the invention by means of pipe conduits.

DETAILED DESCRIPTION OF THE INVENTION

The interconnection according to the invention will be explained below with reference to FIG. 1.

The reactors A and B are connected with each other via the illustrated pipe conduit system. Pipe fittings, such as for example valves, are not shown. Through supply conduit 1, the educt mixture consisting of a liquid fatty acid ester and hydrogen is introduced into the system and into one of the reactors with a pressure in the range from 75 to 100 bar and a temperature of e.g. 180° C. The reactors each contain two catalyst fixed beds, K1 to K4. On trickling through the catalyst fixed beds, the educt mixture is converted into a product mixture consisting of fatty alcohol and hydrogen. The hydrogenation proceeds exothermally and leads to a temperature rise in the mixture and in the reaction zone of the catalyst bed. Temperature measuring devices, TI, installed in the reactors reveal the course of the temperature along the length of the fixed bed and hence the traveling of the reaction zone through the fixed bed. In the production mode of the plant the mixture is passed on through the transfer conduit 2 into the respective downstream reactor. The product mixture leaves the system for the further treatment in the plant via conduit 4. In the case of the catalyst exchange in one of the reactors, the conduit system also allows to guide the flow of the mixture such that it only flows through one of the reactors and thereafter is guided directly to the further treatment.

Via conduits 5, 6 and 7 quench hydrogen can be introduced into the educt/product mixture.

The following Example 1 shows how the quantity of circulated hydrogen can be reduced by using the quench hydrogen:

Example 1

In the hydrogenation of a $C_{16}/C_{18}$ wax ester fraction a reactor inlet temperature of 180° C. and a maximum heating of 30° C. must be maintained. For this purpose, the fatty acid ester (1a) is mixed with fresh hydrogen (1b) and cycle hydrogen (1c) and introduced into the hydrogenation reactor with four catalyst beds. The product (4) chiefly consists of fatty alcohol and hydrogen. The results were determined by means of process simulation.

Without quench gas cooling, a cycle hydrogen quantity of 6834 kg per 25000 kg/h of wax ester is supplied to the reactor, whereas with quench gas cooling the cycle hydrogen quantity ($H_{2,cycle}$+sum $H_{2,quench}$) can be reduced to 3621 kg/h per 25000 kg/h of wax ester.

| Stream | Name | Without quench gas cooling | | With quench gas cooling | |
|---|---|---|---|---|---|
| | | Mass flow kg/h | Temperature ° C. | Mass flow kg/h | Temperature ° C. |
| 1a | Fatty acid ester | 25000 | 232 | 25000 | 232 |
| 1b | $H_{2,\ fresh}$ | 225 | 60 | 225 | 60 |
| 1c | $H_{2,\ cycle}$ | 6834 | 151 | 2676 | 105 |
| 4 | Product | 32059 | 210 | 28846 | 210 |
| 5 | $H_{2,\ quench\ 1}$ | — | — | 718 | 75 |
| 6 | $H_{2,\ quench\ 2}$ | — | — | 189 | 75 |
| 7 | $H_{2,\ quench\ 3}$ | — | — | 38 | 75 |
| Sum $H_2$ (Streams 2 + 3 + 5 + 6 + 7) | | 6834 | | 3621 | |
| TI1 | Bed 1 head | — | 180 | — | 180 |
| TI2 | Bed 1 bottom | — | 200 | — | 210 |
| TI3 | Bed 2 head | — | 200 | — | 199 |
| TI4 | Bed 2 bottom | — | 208 | — | 210 |
| TI5 | Bed 3 head | — | 208 | — | 207 |
| TI6 | Bed 3 bottom | — | 208 | — | 210 |
| TI7 | Bed 4 head | — | 210 | — | 209 |
| TI8 | Bed 4 bottom | — | 210 | — | 210 |

Example 2 shows the dependence of the content of hydrocarbons in the product on the reaction temperature at which the hydrogenation proceeds:

Example 2

In the hydrogenation of a wax ester the content of hydrocarbons in dependence on the reaction temperature was determined experimentally (Table 1). Up to a reactor temperature of 200° C. the hydrocarbon content lies below 0.05 wt-%. Above a temperature of 200° C. the hydrocarbon content rises distinctly.

TABLE 1

| Reaction temperature [° C.] | Hydrocarbon content in the product [wt-%] |
|---|---|
| 170 | 0 |
| 180 | 0.01 |
| 190 | 0.02 |
| 200 | 0.03 |
| 210 | 0.16 |
| 215 | 0.26 |
| 220 | 0.54 |

INDUSTRIAL APPLICABILITY

The invention provides a plant which can continue to produce without interruption also during the exchange of the catalyst, and which provides for optimizing the utilization of the catalyst. The invention therefore is industrially applicable.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 1a supply conduit for fatty acid ester
1b inlet for fresh hydrogen
1c inlet for recirculated hydrogen
2 transfer conduit
3 vacant
4 discharge conduit for product mixture
5 quench hydrogen supply
6 quench hydrogen supply
7 quench hydrogen supply
A reactor
B reactor
K1 catalyst fixed bed
K2 catalyst fixed bed
K3 catalyst fixed bed
K4 catalyst fixed bed
TI1 to TI8 temperature measuring device

The invention claimed is:

1. A process for the continuous production of a fatty alcohol from a fatty acid ester by catalytic trickle-bed hydrogenation, the process comprising the steps of:
   a) mixing the fatty acid ester with hydrogen to produce an educt mixture, wherein the hydrogen comprises fresh hydrogen and recirculated hydrogen, wherein the educt mixture is at a pressure in the range from 50 to 250 bar;
   b) heating the educt mixture to a temperature in the range from 150 to 250° C.;
   c) passing the educt mixture through a first shaft reactor and then through a second shaft reactor, wherein each of the first shaft reactor and the second shaft reactor contain at least one catalyst fixed bed designed as trickle bed, wherein the educt mixture is converted, within a traveling reaction zone, into a liquid product mixture which contains fatty alcohol, hydrogen and, depending on the fatty acid ester used, also further alcohols wherein each catalyst fixed bed has a bed length;

d) measuring a temperature profile along the bed length of each catalyst fixed bed;
e) determining the location of the traveling reaction zone within the catalyst fixed beds by the measured temperature profile from step d);
f) cooling the liquid product mixture;
g) separating the hydrogen from the liquid product mixture to form a hydrogen stream and a liquid product stream containing fatty alcohol;
h) using at least a portion of the hydrogen stream to provide the recirculated hydrogen of step a); and
i) discharging the liquid product stream containing fatty alcohol from the process for the further treatment;
wherein, upon a determination that the traveling reaction zone has entered the catalyst fixed bed of the second shaft reactor and has progressed to such an extent that an inactive zone, which is of sufficient length to provide a protection zone for trapping catalyst poisons, has formed upstream the traveling reaction zone in the catalyst fixed bed of the second shaft reactor, the process further comprises the steps of:
  i. switching the flow of the educt mixture to first flow into the second shaft reactor without first flowing through the first shaft reactor, thereby taking the first shaft reactor out of operation;
  ii. replacing the catalyst fixed bed of the first shaft reactor with fresh catalyst; and
  iii. fluidly connecting the first shaft reactor downstream of the second shaft reactor, thereby placing the first shaft reactor back in operation.

2. The process according to claim 1, wherein the fatty acid ester is a wax ester, and before process step b) the fatty acid ester is passed through a depressurizing device, thereby reducing the content of free fatty acids and other compounds of higher volatility.

3. The process according to claim 2, wherein the depressurizing device is operated at pressures between 1 and 1000 mbar.

4. The process according to claim 2, wherein the depressurizing device is operated at pressures between 10 and 700 mbar.

5. The process according to claim 1, wherein step b) is at a pressure between 75 to 100 bar.

6. The process according to claim 1, wherein the mixture is heated to a temperature in step c) between 180 to 250° C.

* * * * *